United States Patent [19]

Ryan et al.

[11] Patent Number: 4,692,437
[45] Date of Patent: Sep. 8, 1987

[54] ANTI-HYPERTENSIVE AGENTS

[75] Inventors: James W. Ryan; Alfred Chung, both of Miami, Fla.

[73] Assignee: University of Miami, Coral Gables, Fla.

[21] Appl. No.: 156,749

[22] Filed: Jun. 5, 1980

Related U.S. Application Data

[63] Continuation-in-part of Ser. No. 116,951, Jan. 30, 1980, abandoned, Ser. No. 116,950, Jan. 30, 1980, Ser. No. 64,897, Aug. 14, 1979, Ser. No. 64,898, Aug. 14, 1979, Ser. No. 64,899, Aug. 14, 1979, Ser. No. 64,900, Aug. 14, 1979, Ser. No. 64,901, Aug. 14, 1979, Ser. No. 64,902, Aug. 14, 1979, and Ser. No. 64,903, Aug. 14, 1979, said Ser. No. 116,950, is a continuation of Ser. No. 941,289, Sep. 11, 1978, abandoned.

[51] Int. Cl.$^4$ .................. A61K 31/425; A61K 31/40; C07D 207/00; C07D 277/04
[52] U.S. Cl. .................... 514/165; 548/531; 548/535; 548/188; 514/423
[58] Field of Search ............ 260/112.5; 424/177; 548/531, 535, 188; 546/310; 514/165, 423

[56] References Cited

U.S. PATENT DOCUMENTS

| | | | |
|---|---|---|---|
| 3,832,337 | 8/1974 | Ondetti | 260/112.5 |
| 3,891,616 | 6/1975 | Ondetti | 260/112.5 |
| 3,947,575 | 3/1976 | Ondetti | 424/177 |
| 4,046,889 | 9/1977 | Ondetti | 424/319 X |
| 4,052,511 | 10/1977 | Cushman | 424/274 |
| 4,053,651 | 10/1977 | Ondetti | 424/319 X |
| 4,070,361 | 1/1978 | Petrillo | 260/293.85 |
| 4,091,024 | 5/1978 | Ondetti | 260/293.63 |
| 4,105,776 | 8/1978 | Ondetti | 424/274 |
| 4,105,789 | 8/1978 | Ondetti | 424/309 |
| 4,108,886 | 8/1978 | Ondetti | 260/455 R |
| 4,113,715 | 9/1978 | Ondetti | 424/274 |
| 4,116,962 | 9/1978 | Ondetti | 260/293.63 |
| 4,129,566 | 12/1978 | Ondetti | 546/326 |
| 4,146,611 | 3/1979 | Ondetti | 424/177 |
| 4,151,172 | 4/1979 | Ondetti | 260/326.2 |
| 4,154,840 | 5/1979 | Ondetti | 424/267 |
| 4,154,934 | 5/1979 | Bernstein | 546/189 |
| 4,154,935 | 5/1979 | Ondetti | 546/189 |
| 4,154,937 | 5/1979 | Cushman | 546/221 |
| 4,168,267 | 9/1979 | Petrillo | 260/326.2 |

OTHER PUBLICATIONS

Cushman et al., Biochemistry, vol. 16, 1977, p. 5484.
Cushman et al., Experientia, vol. 29, 1973, p. 1032.
Ondetti et al., Science, vol. 196, 1977, p. 441.
Dorer et al., Biochim Biophys. Acta, vol. 429, 1976, p. 220.
Fisher et al., Arch. Biochem. Biophys., vol. 189, 1978, p. 81.
Gavras, et al., N.E. J. Med., vol. 291, 1974, p. 817.
Gavras et al., N.E. J. Med., vol. 298, 1978, p. 991.
Lipmann, Accounts Chem. Res., vol. 6, 1973, p. 6.
Lehninger, Biochemistry, Worth Pub. N.Y., 1970, pp. 153-157.
Fischer et al., Ber. vol. 33, 1900, pp. 2383-2393.

Fischer et al., FEBS Letters, vol. 107, 1979, pp. 273-275.
Cronyn et al., J. Am. Chem. Soc., 74, 4726 (1952).
Lehninger, A., Biochemistry, Worth Publications, Inc., New York (1975), pp. 189-195.
Ryan, J. W. et al., Biochem. J. 167, 501 (1977).
Ryan, J. W. et al., Tissue and Cell 10, 555 (1978).
Methoden der Organischen Chem. (Houben-Weyl), vol. XV, Part I, pp. 376 et seq. (1974).
Carter et al., J. Biol. Chem., 138, 627 (1941).
Engel et al., Proc. Soc. Exp. Biol. Med. 143, 483 (1973).
Jager et al., Chem. Ber. 103, 1727 (1970).
Klosterman et al., Biochem. 6, 170 (1967).
Lijinski et al., Tetrahedron 26, 5137 (1970).
Nagasawa et al., J. Med. Chem. 16, 583 (1973).
Mita et al., Chem. Pharm. Bull. 26 (4), 1333-1335 (1978).
Pfister et al., J. Am. Chem. Soc. 71, 1096 (1949).
Merrifield, Adv. Enzymol 32, 221 (1969).
Ricci et al., Anal. Biochem. 79, 610 (1977).
Cushman et al., Fed. Proc. 38, 2778 (1979).
Cheung et al., J. Biol. Chem. 255, 401 (1979).
Oparil et al., Circ. Res. 32, 415 (1973).

(List continued on next page.)

Primary Examiner—Delbert R. Phillips

[57] ABSTRACT

Inhibitors of angiotensin converting enzyme which are physiologically acceptable salts of compounds which have the formula:

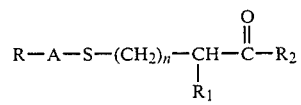

wherein
R is hydrogen, formyl, acetyl, propanoyl, butanoyl, phenylacetyl, phenylpropanoyl, benzoyl, cyclopentanecarbonyl, tert-butyloxycarbonyl, cyclopentanecarbonyl-L-lysyl, pyro-L-glutamyl-L-lysyl, L-lysyl, L-arginyl or pyro-L-glutamyl;
A is phenylalanyl, glycyl, alanyl, tryptophyl, tyrosyl, isoleucyl, leucyl, histidyl, or valyl, the α-amino group thereof being in amide linkage with R;
$R_1$ is hydrogen or methyl;
$R_2$ is L-proline, L-3,4-dehydroproline, D,L-3,4-dehydroproline, L-3-hydroxyproline, L-4-hydroxyproline, L-thiazolidine-4-carboxylic acid, or L-5-oxoproline, the imino group thereof being in imide linkage with the adjacent

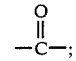

and,
n is 0 or 1, such that when n is 0, $R_1$ is methyl are disclosed as useful anti-hypertensive agents.

8 Claims, No Drawings

OTHER PUBLICATIONS

Oparil et al., *Circ. Res. 29*, 682 (1971).
Dorer et al., *Biochem. J.* 141, 915 (1974).
Sharpless, S. K., "Hypnotics and Sedatives", *The Pharmacological Basis of Therapeutics*, The MacMillan Co. (1965), pp. 105–128.
Kripalani, K. J. et al., *Abstracts, Joint Meeting of ASPET/SOT,* Aug. 13–17, 1978.
Singhvi, S. M. et al., *Abstracts, Joint Meeting of ASPET/SOT,* Aug. 13–17, 1978.
Wong, K. K. and Dreyfuss, J. *Abstracts, Joint Meeting of ASPET/SOT,* Aug. 13–17, 1978.
Buxton et al., *J. Chem. Soc.,* p. 366 (1954).

ANTI-HYPERTENSIVE AGENTS

CROSS REFERENCES TO RELATED APPLICATIONS

This application is a continuation-in-part of each of seven applications filed Aug. 14, 1979 bearing Ser. Nos. 64,897; 64,898; 64,899; 64,900; 64,901; 64,902 and 64,903, all of which are incorporated by reference herein. It is also a continuation-in-part of each of (a) U.S. Ser. No. 116,950 filed Jan. 30, 1980 which is a continuation of Ser. No. 941,289 filed Sept. 11, 1978, and now abandoned, and (b) U.S. Ser. No. 116,951 filed Jan. 30, 1980 and now abandoned in favor of its continuation, pending U.S. Ser. No. 295,589 filed Aug. 24, 1981, which was a continuation of Ser. No. 958,180 filed Nov. 6, 1978, now abandoned; both of which are also incorporated herein by reference.

Ser. No. 116,951 has been abandoned in favor of its continuation Ser. No. 295,589, filed Aug. 24, 1981, which has been abandoned in favor of its continuation, Ser. No. 524,204, filed Aug. 18, 1983, which has been abandoned in favor of its continuation, Ser. No. 680,541, filed Dec. 11, 1984, which has been abandoned in favor of its now pending continuation, Ser. No. 850,055, filed Apr. 10, 1986.

BACKGROUND OF THE INVENTION

Angiotensin converting enzyme (peptidyldipeptide hydrolase, hereinafter referred to as ACE) occupies a central role in the physiology of hypertension. The enzyme is capable of converting the decapeptide angiotensin I, having the sequence AspArgValTyrIleHisProPheHisLeu to an octapeptide, angiotensin II, by removal of the carboxyterminal HisLeu. The symbols for various chemical entities have the meaning given in the following table unless otherwise indicated:

Ala=L-alanine
Arg=L-arginine
Asp=L-aspartic acid
Boc=t-butyloxycarbonyl
Glu=glutamic acid
<Glu=pyro-L-glutamic acid (L-5-oxo-proline)
Gly=glycine
Hip=Hippuric acid (benzoyl-glycine)
His=L-histidine
Ile=L-isoleucine
Leu=L-leucine
Phe=L-phenylalanine
Pro=L-proline
ΔPro=L-3,4-dehydroproline
Ser=L-serine
Trp=L-tryptophan
Tyr=L-tyrosine
Val=L-valine
ACE=Angiotensin converting enzyme
Hepes=N-2-hydroxyethylpiperazine-N'-2-ethanesulfonic acid Angiotensin I is formed by the action of the enzyme renin, an endopeptidase found in kidney, other tissues and plasma, acting on a serum α-2 globulin.

Blood pressure is affected by certain peptides found in the blood. One of these, angiotensin II, is a powerful pressor (blood pressure elevating) agent. Another, bradykinin, a nonapeptide with the sequence ArgProProGlyPheSerProPheArg is a powerful depressor (blood pressure lowering) agent. In addition to a direct pressure effect, angiotensin II stimulates release of aldosterone which tends to elevate blood pressure by causing retention of extracellular salt and fluids. Angiotensin II is found in measurable amount in the blood of normal humans. However, it is found at elevated concentrations in the blood of patients with renal hypertension.

The level of ACE activity is ordinarily in excess, in both normal and hypertensive humans, of the amount needed to maintain observed levels of angiotensin II. However it has been found that significant blood pressure lowering is achieved in hypertensive patients by treatment with ACE inhibitors. [Gravras, I., et al., *New Engl. J. Med.* 291, 817 (1974)].

ACE is a peptidyldipeptide hydrolase. It catalyzes the hydrolysis of the penultimate peptide bond at the C-terminal end of a variety of acylated tripeptides and larger polypeptides having an unblocked α-carboxyl group. The action of ACE results in hydrolytic cleavage of the penultimate peptide bond from the carboxylterminal end yielding as reaction products a dipeptide and a remnant.

The reactivity of the enzyme varies markedly depending on the substrate. At least one type of peptide bond, having the nitrogen supplied by proline, is not hydrolyzed at all. The apparent Michaelis constant (Km) varies from substrate to substrate over several orders of magnitude. For general discussion of the kinetic parameters of enzyme catalyzed reactions, see Lehninger, A., *Biochemistry*, 2nd Ed., Worth Publishers, Inc., New York, 1975, pp. 189–195. Many peptides which are called inhibitors of the enzymatic conversion of angiotensin I to angiotensin II are in fact substrates having a lower Km than angiotensin I. Such peptides are more properly termed competitive substrates. Examples of competitive substrates include bradykinin, and the peptide $BPP_{5a}$ (also called SQ20475) from snake venom, whose sequence is <GluLysTrpAlaPro.

Numerous synthetic peptide derivatives have been shown to be ACE inhibitors by Ondetti, et al. in U.S. Pat. No. 3,832,337 issued Aug. 27, 1974.

The role of ACE in the pathogenesis of hypertension has prompted a search for inhibitors of the enzyme that could act as antihypertensive drugs. See for example U.S. Pat. Nos. 3,891,616; 3,947,575; 4,052,511 and 4,053,651. A highly effective inhibitor, with high biological activity when orally administered, is D-3-mercapto-2-methylpropanoyl-L-proline, designated SQ14225, disclosed in U.S. Pat. No. 4,046,889 to Ondetti et al., issued Sept. 6, 1977, and in scientific articles by Cushman, D. W. et al., *Biochemistry* 16, 5484 (1977), and by Ondetti, M. et al., *Science* 196, 441 (1977). The inhibitor SQ14225 reportedly has an $I_{50}$ value of $2.3 \times 10^{-8}$M. The $I_{50}$ value reported by Cushman, et al., supra is the concentration of inhibitor required to produce 50% inhibition of the enzyme under a standard assay system containing substrate at a level substantially above $K_m$. It will be understood that $I_{50}$ values are directly comparable when all potential factors affecting the reaction are kept constant. These factors include the source of enzyme, its purity, the subtrate used and its concentration, and the composition of the assay buffer. All $I_{50}$ data reported herein have been performed with the same assay system and same enzyme (human urinary ACE) and with an approximately ½ $K_m$ level of substrate and are therefore internally consistent. Discrepancies with data obtained by other workers may be observed. Indeed such discrepancies do exist in the literature, for unknown reasons. See, for example, the $I_{50}$ values for $BPP_{9a}$ reported by Cushman, D. W., et al., *Experientia* 29, 1032 (1973) and by Dorer, F. E., et al., *Biochim. Biophys. Acta* 429, 220 (1976).

The mode of action of SQ14225 has been based upon a model of the active site of ACE developed by analogy with the better known related enzyme, carboxypeptidase A. The active site was postulated to have a cationic site for binding the carboxyl end group of the substrate and a pocket or cleft capable of binding the side chain of the C-terminal amino acid and providing especially tight binding for the heterocyclic ring of a terminal proline residue. A similar pocket for the penultimate amino acid residue was postulated, and the published data suggested a rather stringent steric requirement, since the D-form of the inhibitor was substantially more potent than its stereoisomer or the 3-methyl and unsubstituted analogs. The sulfhydryl group on the inhibitor, postulated to be bound at the active site near the catalytic center, was believed to play a central role in inactivation of the enzyme by combining with the zinc moiety known to be essential for catalytic activity. Substituents on the sulfhydryl, such as a methyl group, and an S-acetyl derivative, substantially reduced potency of the inhibitor. See Cushman, D. W., et al., *Biochemistry*, supra.

In vitro study of the mechanism by which SQ14225 and its analogs act to inhibit ACE has been somewhat hampered by the instability of these molecules under ambient conditions. For example, it has been observed that a fresh aqueous solution of concentration, e.g., 1 mg per ml of SQ14225 at a pH of about 8 becomes substantially less active upon standing for as little as 30 minutes, and that activity continues to decrease as the solution stands for longer periods. It is believed that this loss in activity is mainly the result of dimerization of SQ14225 occurring at the sulfhydryl end groups, whereby a disulfide is formed which is largely inactive as an inhibitor. Since the free sulfhydryl group is highly reactive and may be readily oxidized to polar acidic moieties such as sulfone and sulfoxide groups, it may also be that the observed in vitro loss of activity of aqueous solutions of SQ14225 on standing is in some part a consequence of one or more such oxidation reactions, with formation of a sulfone or sulfoxide which does not function effectively as an inhibitor for ACE.

Such reports of SQ14225 clinical testing as are currently available, some of which refer to the compound under the name "Captopril", suggest that the product is sufficiently stable in the normal gastric and intestinal environments of most patients to be an effective inhibitor for ACE when administered orally. It is not yet clear, however, whether there may be a group of patients for which SQ14225 is substantially ineffective. Because of the high reactivity of the free sulfhydryl group, SQ14225 could readily form mixed disulfides with serum, cellular proteins, peptides or other free sulfhydryl group-containing substances in the gastric or intestinal environments, in addition to the possibility for dimer formation or oxidative degradation reactions. A mixed disulfide with protein may be antigenic and, indeed, occasional allergic reactions have been clinically observed. See Gavras, et al, *New England J. Med.* 298, 991 (1978). Disulfides and oxidative degradation products of SQ14225, if formed, may at best be expected to be largely ineffective as inhibitors. It may be postulated accordingly that dose response to SQ14225 may vary with conditions of administration and among individual patients. Moreover, in at least some patients, unwanted side effects may occur and maintenance of an effective concentration of the inhibitor in the body may be difficult to control.

Thioester compounds generally are thought to be highly reactive in that the thioester linkage is readily hydrolyzable to a sulfhydryl moiety and a carboxylic moiety. Thioesters are accordingly often used as active ester intermediates for acylation under mild conditions. Such groups as, e.g., acetylthio have been used as blocking groups in the above cited Ondetti, et al. patents. Thioester intermediates are also postulated to occur in the biosynthesis of cyclic peptides such as tyrocidin or gramicidin S. See Lipmann, F. in *Accounts Chem. Res.* 6, 361 (1973).

Thioester compounds having potent ACE inhibitory activity and oral effectiveness as anti-hypertensive agents have been disclosed in copending applications Ser. No. 116,950, filed Jan. 30, 1980, Ser. No. 116,951, filed Jan. 30, 1980, and Ser. Nos. 064,897 through 064,903, all filed on Aug. 14, 1979. All copending applications are incorporated herein by reference.

Compounds related to SQ14,225 have been disclosed by Ondetti, et al., U.S. Pat. Nos. 4,046,889; 4,052,511; 4,053,651; 5,113,715 and 5,154,840. Of interest are disclosed analogs of SQ14,225 having the five-membered heterocyclic ring of proline replaced by a four- or a six-membered ring. The inhibitory potencies of such analogs relative to SQ14,225 are not disclosed. Substitution of D-proline for L-proline is reported to drastically reduce inhibitory potency of 3-mercaptopropanoyl amino acids (Cushman, D. W., et al., supra).

The substitution of L-3,4-dehydroproline for proline has been studied in several systems. Substitution of L-3,4-ΔPro in the 7 position of bradykinin yields a bradykinin derivative which has significantly reduced physiological activity. See Fisher, G. H. et al., *Arch. Biochem. Biophys.* 189, 81 (1978). On the other hand, substitution of L-3,4-ΔPro at the 3, 5, 8 or 9 position in ACE inhibitor BPP9a enhances its inhibitory activity. See Fisher, G. H. et al., *FEBS Letters* 107, 273 (1979). In copending application Ser. No. 116,951, applicants found that the compounds having ΔPro, which are disclosed in said application, have high inhibitory potency and anti-hypertensive effectiveness. However, at present, no rationale can be advanced to explain the diversity of observed results following substitution of ΔPro for proline. Similarly, no clear picture has emerged of the effects of other proline derivatives or analogs substituted at various loci on ACE inhibitors.

To date, the effect of the amino acid to the left of the sulfur in the thioester compounds disclosed in our copending applications, has not been determined. It is thought that this amino acid functions as an additional recognition site for the enzyme. If this is true, it would be expected that a compound with an amino acid here would be a better inhibitor. Applicants have found that many amino acids, substituted amino acids or analogous compounds can be utilized for A in Formula I below to provide effective anti-hypertensive agents and effective inhibitors of ACE. See copending applications of Ryan, Ser. Nos. 145,772; 145,773; and, 146,107, all filed on May 2, 1980. Applicants have found that the hydroxyprolines, proline, L-, and D,L-3,4-dehydroproline, thiazolidine-4-carboxylic acid, and L-5-oxo-proline derivatives are all effective anti-hypertensive agents and have high inhibitory potency for ACE.

SUMMARY OF THE INVENTION

In copending applications Ser. Nos. 064,897–064,903; 115,950; 116,951 and 121,188, applicants found that compounds according to Formula I were effective anti-hypertensive agents and have high inhibitory potency for ACE. At the time of filing these applications, applicants had not examined any salts of these compounds and thus did not know whether the salts would be effective. Applicants have now prepared salts of these compounds and have determined that they are effective anti-hypertensive agents and potent inhibitors of ACE.

Accordingly, the present invention relates to novel inhibitors of ACE which are basic salts of compounds which have the general formula

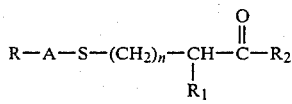

wherein

R is hydrogen, formyl, acetyl, propanoyl, butanoyl, phenylacetyl, phenylpropanoyl, benzoyl, cyclopentanecarbonyl, tert-butyloxycarbonyl, cyclopentanecarbonyl-L-lysyl, pyro-L-glutamyl-L-lysyl, L-lysyl, L-arginyl or pyro-L-glutamyl;

A is phenylalanyl, glycyl, alanyl, tryptophyl, tyrosyl, isoleucyl, leucyl, histidyl, or valyl, the α-amino group thereof being in amide linkage with R;

$R_1$ is hydrogen or methyl;

$R_2$ is L-proline, L-3,4-dihydroproline, D,L-3,4-dehydroproline, L-3-hydroxyproline, L-4-hydroxyproline, L-thiazolidine-4-carboxylic acid, or L-5-oxoproline, the imino group thereof being in imide linkage with the adjacent

and, n is 0 or 1, such that when n is 0, $R_1$ is methyl. The amino acid A may exist in any optical form. That is, A may be in the L-, D- or D,L-form.

All of the above compounds are inhibitors of ACE and are useful as orally effective anti-hypertensive agents.

DESCRIPTION OF THE PREFERRED EMBODIMENTS

The compounds of Formula I form basic salts with various inorganic and organic bases. Such salts include ammonium salts, alkali metal salts, alkaline earth salts, salts with organic bases, salts with amino acids and the like. Examples of alkali metal salts include the sodium or potassium salts. Examples of alkaline earth metal salts include the calcium or magnesium salts. Examples of organic base salts include the benzathine, N-methyl-D-glucamine or hydrabamine salts. Examples of amino acid salts include arginine or lysine. The sodium potassium or lysine salts are preferred. Likewise, non-toxic, physiologically acceptable salts are preferred.

The salts are formed by reacting the free acid of the compounds of Formula I with one equivalent of the appropriate base providing the desired cation in a solvent or medium in which the salt is insoluble, or in water and removing the water by freeze drying.

The salts of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the

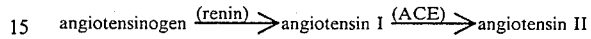

sequence by inhibiting angiotensin converting enzyme and reducing or eliminating the formation of the pressor substance angiotensin II. Thus by the administration of a composition containing one or a combination of salts of the compounds of Formula I, angiotensin dependent hypertension in the species of mammal suffering therefrom is alleviated. A single dose, or preferably two or four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, *Proc. Soc. Exp. Biol. Med.* 143, 483 (1973). The substance is preferably administered orally, but paranteral routes such as subcutaneous, intramuscular, intravenous or intraperitoneal can also be employed.

The salts of this invention can be utilized to achieve the reduction of blood pressure by formulating in compositions such as tablets, capsules or elixirs for oral administration or in sterile solutions or suspensions for parenteral administration. About 10 to 500 mg. of a salt or mixture of salts of the compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, and the like can be incorporated as required.

A more complete appreciation of the invention will be realized by references to the following specific examples which describe the details of the preparation and operational effectiveness of the foregoing salts. The following examples are not intended to limit the invention disclosed herein except to the extent that limitations are specifically stated or to the extent to which limitations appear in the appended claims.

EXAMPLE 1

Preparation of the sodium salt of $N^\alpha$-[3-($N^\alpha$-benzoyl-D,L-phenylalanylthio)-2-D-methylpropanoyl]-L-proline $NaHCO_3$ (0.5 mmol of a 1M solution) was added to 234.3 mg (0.5 mmol) of $N^\alpha$-[3-(Bz-D,L-phenylalanylthio)-2-D-methylpropanoyl]-L-proline in 1 ml of absolute ethanol with stirring. Solvents were removed with a rotary evaporator at approximately 35° C. Fresh ethanol was added to the oily residue and again solvent was removed with the rotary evaporator. The procedure was repeated once more with absolute alcohol and then twice with benzene. The white residue was dried in a vacuum desiccator over $P_2O_5$. Recrystallization from 95% ethanol and benzene yielded 135 mg (55.1% yield) of white crystals having a decomposition point of 185°–186° C. (softens at 153° C.). Infrared analysis using a KBr pellet showed zwitterion bands at 1398 and 1600 $cm^{-1}$ and a thio ester band at 1682 $cm^{-1}$. Paper electrophoresis at pH 2 and 5 and thin layer chromatography (silica gel plates) using three separate solvent systems showed only one spot detectable under UV light at short wavelength after reaction with phenazine methosulfate reagents.

Elemental analysis: Calc. for $C_{25}H_{27}N_2SNaO_5 \cdot 2H_2O$: Calc.: C=57.02; H=5.93; N=5.32; S=6.09. Found: C=56.37; H=5.59; N=5.30; S=5.99.

EXAMPLE 2

Preparation of the potassium salt of $N^\alpha$-[3-($N^\alpha$-benzoyl-D,L-phenylalanylthio)-2-D-methylpropanoyl]-L-proline The potassium salt of the named compound was prepared by following the procedure of Example 1 using 1M $KHCO_3$ in place of the 1M $NaHCO_3$. Recrystallization yielded 70 mg of a white solid having a decomposition point of 132°–134° C. Infrared analysis, paper electrophoresis, and thin layer chromatography yielded values identical to those of the corresponding sodium salt from Example 1.

EXAMPLE 3

Preparation of the L-lysine salt of $N^\alpha$-[3-($N^\alpha$-benzoyl-D,L-phenylalanylthio-2-D-methylpropanoyl]-L-proline A solution of 73.1 mg (0.5 mmole) of L-lysine free base in 0.3 ml of deionized water was added drop wise, with stirring, to a solution of 234.3 mg (0.5 mmole) of $N^\alpha$-[3-($N^\alpha$-benzoyl-D,L-phenylalanylthio)-2-D-methylpropanoyl]-L-proline in 1 ml of absolute alcohol. Solvents were removed with a rotary evaporator to yield a white residue. Fresh absolute alcohol was added and again solvent was removed with a rotary evaporator. The procedure was repeated two more times with absolute alcohol and then twice with benzene. The final yield was 0.292 g (dp 152°–154.4° C.) after drying in a vacuum desiccator over $P_2O_5$. Recrystallization from absolute alcohol, a few drops of water and benzene gave a yield of 141 mg of a white precipitate having a decomposition point of 162.5°–163.5° C. (softened at 160° C.). Infrared analysis using a KBr pellet showed zwitterion bands at 1389 and 1620 $cm^{-1}$, carbonyl of amide band at 1641 $cm^{-1}$ and a thio ester band at 1678 $cm^{-1}$. Paper electrophoresis at pH 5 and thin layer chromatography (silica gel plates) using three separate solvent systems showed the presence of both the named compound and lysine.

Additional physiologically acceptable salts can be prepared by substituting the appropriate base for the $NaHCO_3$, $KHCO_3$ or lysine in Examples 1–3 and substantially following the procedures described below. Although Examples 1–3 described the preparation of the salts of the compound $N^\alpha$-[3-($N^\alpha$-benzoyl-D,L-phenylalanylthio)-2-D-methylpropanoyl]-L-proline, it will be understood that physiologically acceptable salts of any compound described by Formula I can be prepared in the same manner.

EXAMPLE 4

Oral Effectiveness of the sodium salt of $N^\alpha$-[3-($N^\alpha$-benzoyl-D,L-phenylalanylthio)-2-D-methylpropanoyl]-L-proline Rats (150–190 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 ng/kg of angiotensin I in 20 $\mu$l of 0.9 g % NaCl; an amount of angiotensin I sufficient to raise mean arterial blood pressure by 45 mm Hg. After the responsiveness of a given rat to angiotensin I was established, the named compound at 10 $\mu$mol/kg (drug dissolved in 0.15 ml of $H_2O$ plus 10 $\mu$l of 1N $NaHCO_3$), was given via a stomach tube. At timed intervals, the effects of 400 ng/kg of angiotensin I on mean arterial blood pressure were tested. Results are shown below:

| Time after Oral Administration (Minutes) | Blood Pressure Response to 400 ng/kg of Angiotensin I (% of Control) |
| --- | --- |
| −5 | 100% (45 mm Hg) |
| +5 | 82 |
| 10 | 33 |
| 15 | 24 |
| 20 | 27 |
| 30 | 27 |
| 40 | 22 |
| 50 | 24 |
| 60 | 27 |
| 90 | 36 |
| 120 | 44 |
| 150 | 62 |
| 180 | 60 |
| 210 | 71 |
| 240 | 73% |

EXAMPLE 5

Intravenous Effectiveness of the potassium salt of N$^\alpha$-[3-(N$^\alpha$-benzoyl-D,L-phenylalanylthio)-2-D-methylpropanoyl]-L-proline The intravenous effectiveness of the named compound was examined by following the procedure described in Example 4 except that 1 μmole/Kg of the drug was given intravenously. The results are shown below:

| Time After IV Administration (Minutes) | Blood Pressure Response to 400 ng/kg of Angiotensin I (% of Control) |
|---|---|
| −5 | 100% (54 mm Hg) |
| +5 | 46 |
| 10 | 37 |
| 15 | 41 |
| 20 | 37 |
| 30 | 44 |
| 40 | 50 |
| 50 | 39 |
| 60 | 46 |
| 90 | 52 |
| 120 | 59% |

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A new compound comprising physiologically acceptable salts of compounds having the formula

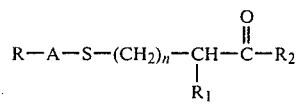

wherein

R is hydrogen, formyl, acetyl, propanoyl, butanoyl, phenylacetyl, phenylpropanoyl, benzoyl, cyclopentanecarbonyl, tert-butyloxycarbonyl, cyclopentanecarbonyl-L-lysyl, pyro-L-glutamyl-L-lysyl, L-lysyl, L-arginyl or pyro-L-glutamyl;

A is phenylalanyl, glycyl, alanyl, tryptophyl, tyrosyl, isoleucyl, leucyl, histidyl or valyl, the α-amino group thereof being in amide linkage with R unless R is hydrogen;

$R_1$ is hydrogen or methyl;

$R_2$ is a residue of L-proline, L-3,4-dehydroproline, D,L-3,4-dehydroproline, L-3-hydroxyproline, L-4-hydroxyproline, L-thiazolidine-4-carboxylic acid, or L-5-oxo-proline, the imino group thereof being in imide linkage with the adjacent

and, n is 0 or 1, such that when n is 0, $R_1$ is methyl.

2. A compound of claim 1 wherein said salt is selected from the group comprising sodium, potassium, calcium, magnesium, benzathine, hydrabamine, N-methyl-D-glucamine, arginine or lysine.

3. A compound of claim 1 wherein said salt is sodium.

4. A compound of claim 1 wherein said salt is potassium.

5. A compound of claim 1 wherein said salt is lysine.

6. A compound of claim 2, 3, 4 or 5 wherein R is benzoyl, A is phenylalanyl, $R_1$ is methyl, $R_2$ is L-proline and n is 1.

7. A method for inhibiting angiotensin converting enzyme in vivo comprising administering an effective oral dose of an inhibitor of claim 1.

8. A method for reducing blood pressure in vivo comprising administering an effective oral dose of an inhibitor of claim 1.

* * * * *

UNITED STATES PATENT AND TRADEMARK OFFICE
CERTIFICATE OF CORRECTION

PATENT NO. : 4,692,437

DATED : September 8, 1987

INVENTOR(S) : James W. Ryan and Alfred Chung

It is certified that error appears in the above-identified patent and that said Letters Patent is hereby corrected as shown below:

Cover Page, Col 1 - after "[73] assignee..."

Insert the following:

-- [*] Notice: The portion of the term of this patent subsequent to Sept. 1, 2004 has been disclaimed.--

Cover Page Col. 1 insert the following:

UNITED STATES PATENT AND TRADEMARK OFFICE
CERTIFICATE OF CORRECTION

PATENT NO. : 4,692,437
DATED : September 8, 1987
INVENTOR(S) : James W. Ryan and Alred Chung It is certified that error appears in the above-identified patent and that said Letters Patent is hereby corrected as shown below:

| | | |
|---|---|---|
| 4261895 | 10/1978 | Wiskott |
| 4283407 | 9/1978 | Malen et al. |
| 4248883 | 3/1980 | Sawayama et al. |
| 4216209 | 3/1979 | Bellini et al. |
| 4179568 | 7/1978 | Cohen et al. |
| 4288368 | 7/1979 | Haugwitz |
| 4299769 | 4/1980 | McEvoy |
| 3973006 | 2/1975 | Ondetti |
| 3976770 | 2/1975 | Bumpus |
| 4254267 | 10/1979 | Rovnyak |
| 4252943 | 1/1980 | Krapcho |
| 4241076 | 5/1979 | Ondetti et al. |
| 4237129 | 6/1979 | Ondetti et al. |
| 4237134 | 6/1979 | Ondetti et al. |
| 4234489 | 6/1979 | Ondetti et al. |
| 4221912 | 8/1979 | Ondetti et al. |
| 4221804 | 9/1979 | Rovnyak |
| 4217458 | 8/1979 | Ondetti |

UNITED STATES PATENT AND TRADEMARK OFFICE
CERTIFICATE OF CORRECTION

PATENT NO. : 4,692,437
DATED : September 8, 1987
INVENTOR(S) : James W. Ryan and Alfred Chung It is certified that error appears in the above-identified patent and that said Letters Patent is hereby corrected as shown below:

| | | |
|---|---|---|
| 4217359 | 8/1979 | Krapcho |
| 4216209 | 3/1979 | Bellini et al. |
| 4211786 | 3/1979 | Rovnyak |
| 4206137 | 11/1978 | Condon et al. |
| 4206121 | 12/1978 | Ondetti et al. |
| 4199512 | 9/1978 | Ondetti et al. |
| 4198517 | 12/1978 | Ondetti |
| 4198515 | 12/1978 | Ondetti |
| 4198509 | 10/1978 | Losee |
| 4192878 | 5/1978 | Ondetti |
| 4186268 | 1/1979 | Petrillo |
| 4179434 | 6/1978 | Ondetti et al. |
| 4177277 | 9/1978 | Ondetti et al. |
| 4173704 | 5/1978 | Ondetti et al. |
| 4112119 | 3/1977 | Ondetti et al. |
| 4127729 | 2/1978 | Ondetti |
| 4128721 | 3/1978 | Ondetti |
| 4140786 | 3/1978 | Ondetti et al. |
| 4140797 | 3/1978 | Ondetti et al. |

UNITED STATES PATENT AND TRADEMARK OFFICE
CERTIFICATE OF CORRECTION

PATENT NO. : 4,692,437

DATED : September 8, 1987

INVENTOR(S) : James W. Ryan and Alfred Chung

It is certified that error appears in the above-identified patent and that said Letters Patent is hereby corrected as shown below:

| | | |
|---|---|---|
| 4140864 | 3/1978 | Ondetti et al. |
| 4154736 | 2/1978 | Ondetti et al. |
| 4154936 | 3/1978 | Ondetti et al. |
| 4154942 | 8/1978 | Ondetti et al. |
| 4154960 | 6/1978 | Ondetti et al. |
| 4156084 | 8/1978 | Ondetti et al. |
| 4156786 | 6/1978 | Ondetti et al. |
| 4284561 | 12/1979 | Petrillo et al. |
| 4284779 | 10/1977 | Ondetti et al. |
| 4284780 | 5/1978 | Ondetti et al. |
| 4291040 | 10/1979 | Krapcho |
| 4296113 | 1/1980 | Ondetti |
| 4297275 | 2/1980 | Sundeen et al. |
| 4321392 | 2/1980 | Ryono et al. |
| 4339600 | 2/1978 | Ondetti et al. |
| 4154946 | 6/1978 | Ondetti et al. |

UNITED STATES PATENT AND TRADEMARK OFFICE
CERTIFICATE OF CORRECTION

PATENT NO. : 4,692,437
DATED : September 8, 1987
INVENTOR(S) : James W. Ryan and Alfred Chung It is certified that error appears in the above-identified patent and that said Letters Patent is hereby corrected as shown below:

| | | |
|---|---|---|
| 4165320 | 6/1978 | Ondetti et al. |
| 4175199 | 12/1978 | Ondetti et al. |
| 4176235 | 12/1978 | Ondetti et al. |
| 4176291 | 12/1978 | Ondetti et al. |
| 4192945 | 3/1979 | Ondetti |
| 4220791 | 3/1979 | Rovnyak |
| 4225495 | 12/1978 | Ondetti |
| 4235885 | 6/1979 | Sundeen et al. |
| 4263293 | 5/1980 | Sundeen et al. |
| 4282235 | 9/1979 | Ondetti |
| 4483861 | 10/1979 | Iwao |

Foreign Patent Documents:

| | | |
|---|---|---|
| 2457463 | 12/1974 | Fed. Rep. of Germany |
| 2703828 | 1/1977 | Fed. Rep. of Germany |
| 2407204 | 10/1977 | France |
| WO800044 | 4/1980 | PCT-European Patent Appln. |

UNITED STATES PATENT AND TRADEMARK OFFICE
CERTIFICATE OF CORRECTION

PATENT NO. : 4,692,437
DATED : September 8, 1987
INVENTOR(S) : James W. Ryan and Alfred Chung It is certified that error appears in the above-identified patent and that said Letters Patent is hereby corrected as shown below:

| | | |
|---|---|---|
| 2018248 | 10/1979 | UK Application |
| 41632 | 1/1980 | Japanese Application |
| 49657 | 10/1979 | Japanese Application |
| 81116 | 1/1980 | Japanese Application |
| 135093 | 4/1980 | Japanese Application |
| 3973006 | 2/1975 | Ondetti |

Cover Page, Col 2. delete "[45] Date of Patent: Sept. 8, 1987" and insert -- [45] Date of Patent: *Sept. 8, 1987 --

Signed and Sealed this

Ninth Day of May, 1989

*Attest:*

DONALD J. QUIGG

*Attesting Officer*       *Commissioner of Patents and Trademarks*